United States Patent
Boukhny et al.

(10) Patent No.: US 11,580,483 B2
(45) Date of Patent: *Feb. 14, 2023

(54) INTRAOCULAR LENS STORAGE CART AND METHODS

(71) Applicant: Alcon Inc., Fribourg (CH)

(72) Inventors: Mikhail Boukhny, Laguna Niguel, CA (US); David Thoe, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 240 days.

This patent is subject to a terminal disclaimer.

(21) Appl. No.: 17/116,927

(22) Filed: Dec. 9, 2020

(65) Prior Publication Data

US 2021/0090002 A1 Mar. 25, 2021

Related U.S. Application Data (63) Continuation of application No. 16/264,976, filed on Feb. 1, 2019, now Pat. No. 10,891,581, which is a
(Continued)

(51) Int. Cl.
| | | |
|---|---|---|
| *G06Q 10/08* | (2012.01) | |
| *G07F 17/00* | (2006.01) | |
| *A61B 50/10* | (2016.01) | |
| *A61B 50/13* | (2016.01) | |
| *A61B 50/15* | (2016.01) | |
| *A61B 90/96* | (2016.01) | |

(Continued)

(52) U.S. Cl.
CPC ............ *G06Q 10/08* (2013.01); *A61B 50/10* (2016.02); *A61B 50/13* (2016.02); *A61B 50/15* (2016.02); *A61B 90/96* (2016.02); *A61B 90/98* (2016.02); *G07F 17/0092* (2013.01); *G16H 20/13* (2018.01); *G16H 40/20* (2018.01); *G16H 40/63* (2018.01); *A61B 2050/105* (2016.02); *A61B 2050/155* (2016.02); *A61F 2/1691* (2013.01); *A61F 2250/0085* (2013.01)

(58) Field of Classification Search
CPC ........ G06Q 10/08; G16H 40/20; G16H 40/63; A61B 90/98; A61B 90/96; A61B 50/15; A61B 50/13; A61B 50/10; A61B 2050/155; A61B 2050/105; G07F 17/0092; A61F 2250/0085; A61F 2/1691
See application file for complete search history.

(56) References Cited

U.S. PATENT DOCUMENTS

2008/0065264 A1* 3/2008 Omura .................. A61B 90/96
700/231

FOREIGN PATENT DOCUMENTS

| JP | H105246 A | 1/1998 |
| JP | 201712419 A | 1/2017 |
| WO | WO-2005084155 A2 * | 9/2005 |

OTHER PUBLICATIONS

Salgado, Miguel Galve. Impact of medical equipment tracking in a health care system. ProQuest Dissertations and Theses. ProQuest Dissertations Publishing. (2006)) (Year: 2006).*

* cited by examiner

*Primary Examiner* — Linh Giang Le (57) ABSTRACT

Systems, apparatuses, and methods include an intraocular lens (IOL) cart that may assist with inventory management and may help users identify an IOL for use in a particular surgical application. The IOL cart may include sensors and indicators that provide information to a user and may update IOL inventory automatically whenever the IOL cart is accessed by a user.

7 Claims, 4 Drawing Sheets

Related U.S. Application Data continuation of application No. 14/880,465, filed on Oct. 12, 2015, now Pat. No. 10,242,332.

(51) Int. Cl.
*A61B 90/98* (2016.01)
*G16H 40/63* (2018.01)
*G16H 40/20* (2018.01)
*G16H 20/13* (2018.01)
*A61F 2/16* (2006.01)

INTRAOCULAR LENS STORAGE CART AND METHODS

TECHNICAL FIELD

This disclosure is directed to a storage consignment cart for surgical applications. More particularly, this disclosure is directed to an intraocular lens consignment cart for surgical applications.

BACKGROUND

Cataract surgery involves removal of the natural lens of the eye and replacing it with an artificial lens commonly referred to as an intraocular lens (IOL). IOLs come in a variety of types, and each is designed to provide a particular corrective power to a user. As a part of creating a surgical plan, a healthcare provider may identify a particular IOL for a patient based on a pre-surgical evaluation. However, an intraoperative evaluation performed during the course of a cataract surgery may result in a modification of the surgical plan to address discrepancies that were not known when the surgical plan was created. An example of modifying the surgical plan occurs when a surgeon performs an intraoperative evaluation and determines that a different IOL may be better suited for the patient than the IOL selected during pre-surgical planning. While such intraoperative evaluations provide benefits including a better patient outcome, such intraoperative changes in plan can create confusion and inefficiency in the operating room. For example, when a new IOL is required in order to complete a surgical procedure, this staff must locate, acquire, and prepare the newly requested IOL for implantation. Furthermore, if the newly indicated IOL is not available in consignment, then the closest lens to the indicated IOL or a competitive product needs to be identified.

In order to reduce inefficiency and confusion during an IOL surgery, surgical staff may sometimes provide a large stack of different potential lenses based on the pre-surgical plan. Surgical staff must allocate the time and resources to manage the lens inventory and transport any newly identified lenses to the operating room theater for implantation.

The present disclosure is directed to a system and method for simplifying access to IOLs during intraoperative evaluations.

SUMMARY

In some exemplary aspects, the present disclosure is directed to an intraocular lens (IOL) cart that may include a base housing configured to receive a plurality of IOL packages. The base housing being configured to detect the presence of individual IOL packages. The IOL cart may also include a computer unit associated with the base housing and configured to receive and store information from the base housing indicative of the presence of individual IOL packages disposed within the base housing. The computer unit may be configured to provide information relating to one or more of the individual IOL packages to a user.

In some aspects, the IOL cart may include one or more sensors configured to detect information relating to individual IOL packages. In some aspects, the one or more sensors may include one of a visual detection method, a barcode scanner, and an RFID scanner. The one or more sensors may be disposed in a position to scan IOL packages as they are introduced to the base housing. In an aspect, the IOL cart may include a movable shelf arranged to carry the plurality of IOL packages, the one or more sensors being positioned above the shelf to detect the IOL packages while the shelf is being closed. In some aspects, the IOL cart may include a plurality of visual indicators actuatable by the computer unit to identify a selected IOL package in the base housing. In an aspect, the base housing may include a shelf divided into rows sized and arranged to receive individual IOL packages. The shelf may include a plurality of separators that divide the shelf into the rows, with each separator having one or more visual indicators usable to identify an IOL package disposed thereon. The visual indicators may be LED lights. In some aspects, the computer unit includes an inventory database configured to store IOL power information and location information within the base housing for each individual IOL package.

In an exemplary aspect, the present disclosure is directed to an IOL package inventory system that includes a plurality of sensors and a computer unit. The plurality of sensors may be configured to read information relating to a product in a product package and detect its storage location. The computer unit may be in communication with the plurality of sensors, and may be configured to store information relating to each product and its location in a database. The computer unit may be arranged to identify a specific product package in response to an input identifying desired parameters of the product.

In an aspect, the product is an intraocular lens, and wherein the product package is an intraocular lens package. In an aspect, the inventory system may include an IOL cart having a plurality of storage locations for individual IOL product packages. The plurality of sensors may be disposed on the IOL cart to detect the storage location of an IOL product package in the IOL cart. The computer unit may be configured to receive input from a user to reserve a specific product package. The plurality of sensors may include visual scanners, RFID sensors, and/or barcode scanners. The computer unit may be configured to send an actuating signal to an indicator adjacent a storage location for a desired product package.

In an exemplary aspect, the present disclosure is directed to a method of tracking inventory that includes storing information relating to an IOL and the location of the IOL package in an IOL cart. A request may be received from a user relating to a desired IOL. The method may include comparing the stored information to the received request to identify an IOL in the inventory most closely matching the desired IOL. The method may also include actuating a visual indicator adjacent the identified IOL.

In an aspect, the method of tracking inventory may include receiving a signal from a sensor identifying a specific IOL package in an IOL cart. In an aspect, the method of tracking inventory may include sensing IOL packages present on a shelf while the shelf is being closed. In an aspect, the method of tracking inventory may include updating an inventory database with information relating to the sensed IOL packages.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

These figures will be better understood by reference to the following detailed description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In addition, this disclosure describes some elements or features in detail with respect to one or more implementations or Figures, when those same elements or features appear in subsequent Figures, without such a high level of detail. It is fully contemplated that the features, components, and/or steps described with respect to one or more implementations or Figures may be combined with the features, components, and/or steps described with respect to other implementations or Figures of the present disclosure. For simplicity, in some instances the same or similar reference numbers are used throughout the drawings to refer to the same or like parts.

The present disclosure relates generally to surgical systems that include an IOL cart that may contain a plurality of different types and sizes of IOLs for use during surgical procedures. The IOL cart provides a central storage location for the variety of IOLs, coupled with intelligence for IOL identification and inventory management. The intelligence on the IOL cart provides up-to-date inventory information based on data that is updated whenever the IOL cart is accessed. As such, the inventory in the IOL cart is always complete and accurate. Further, since the IOL cart may be present in the operating room, a user may have immediate access to a large population of IOLs to, when needed, quickly substitute an IOL that is different than the one identified in the preoperative surgical plan.

In addition to providing up-to-date inventory benefits, the IOL cart may also provide the inventory information to a user, such as a healthcare provider, during a cataract surgery and identify the specific location of the IOL within the IOL cart for quick access the user. For example, if a planned lens power changes as a result of an intraoperative evaluation, the IOL cart may receive confirmation of the change and indicate to a user the availability of an alternative lens with an indicator identifying the particular IOL within the IOL cart. The IOL cart may also recommend and/or identify a closest matching lens in the event that the requested or alternative lens is not available. In some implementations, this information may also include the availability of the lens selection, the lens catalog power family value, or its actual power as indicated on the lens package. In some implementations, this identifying information may be provided either by way of a two dimensional barcode or an RFID tag on or in the IOL packaging.

For lens inventory management, the IOL cart may communicate with other systems making up a part of the surgical system. In some implementations, the IOL cart may provide a user with an overview of consignment lens inventory, and during preoperative assessment, may indicate to the user whether the planned lens (i.e., the lens identified during the preoperative planning stage) and the nearest neighbor lens exist in inventory or need to be ordered.

A number of benefits may be achieved using the IOL cart of the surgical system disclosed herein. For example, the IOL cart may enable users to more efficiently plan and execute cataract surgeries by linking IOL inventory to the planning and intraoperative evaluation process. In some implementations, users, such as healthcare professionals, may benefit from the knowledge and confidence that both the planned and alternative lenses exist in consignment or are placed on order to support the procedure date. Still, additional implementations may optimize patient outcomes by indicating actual lens power instead of only generic labeled power both in the preoperative planning phase as well as during intraoperative evaluation.

Figure 1:
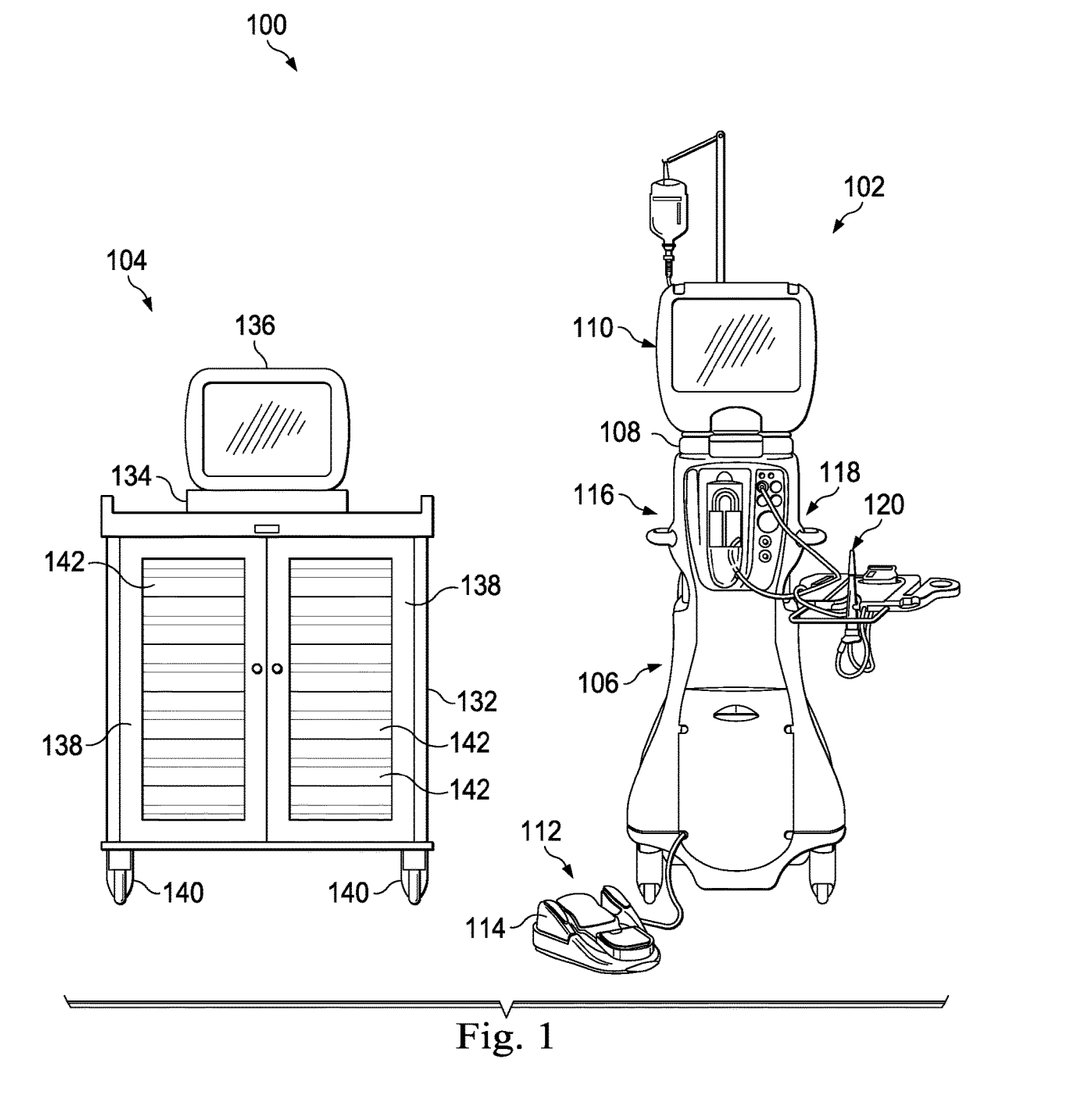
FIG. 1 is an illustration of an exemplary surgical suite of instruments according to an exemplary aspect.

FIG. 1 shows systems that collectively make up a surgical suite 100 of surgical systems. The surgical suite 100 may be arranged to perform a surgical procedure, such as, for example and without limitation, a cataract surgical procedure. In this exemplary implementation, the surgical suite 100 includes a phacoemulsification system 102 and an IOL cart 104. Other implementations may include additional surgical systems that may make up part of the surgical suite 100. For example, some implementations may include an ophthalmic microscope, an image guided system, a laser treatment system, or other system that may add utility and functionality to the capabilities of the surgical suite 100. Yet other surgical systems are contemplated and may make up one or more systems of the surgical suite 100.

The phacoemulsification system 102 may be arranged and configured to permit a user, such as an ophthalmic surgeon, to perform a phacoemulsification procedure as a part of a cataract surgical procedure or an IOL replacement procedure. In this implementation, the phacoemulsification system 102 includes a base housing 106 with a computer unit 108 and an associated display screen 110 configured to show data relating to system operation and performance during use. The phacoemulsification system 102 also includes a number of subsystems that may be used together to perform the surgical procedures. For example, some subsystems of the phacoemulsification system 102 may include, without limitation, a foot pedal subsystem 112 including, for example, a foot pedal 114, a fluidics subsystem 116 including an irrigation source and a flow control vacuum pump that irrigates and aspirates the eye through flexible tubing, an ultrasonic generator subsystem 118 including an ultrasonic oscillation hand piece 120 with a cutting needle. These subsystems may overlap and may cooperate to perform various aspects of the surgical procedure. For example, in some embodiments, an end of an aspiration line of the flexible tubing is associated with the cutting needle of the hand piece 120 to provide irrigation and cooling during the surgical procedure. The phacoemulsification system 102 may be used during a surgical procedure to emulsify and remove a natural lens in preparation for a replacement IOL or may be used during a revision surgery when replacing or changing a previously implanted IOL.

The IOL cart 104 may be arranged to provide simple access to IOL inventory during a cataract surgical procedure. The IOL cart 104 may provide a central storage location for IOLs and may actively track inventory and availability of IOLs. In some instances, the IOL cart 104 with its inventory contained therein, may be transported to or disposed within the surgical room. This may provide easy access to the inventory when an intraoperative evaluation requires a different IOL than the one identified during the pre-surgical evaluation.

Conventionally, IOLs are packaged and marked with a power representing a family diopter power. As used herein, a family power refers to a range of powers falling within traditional designations for IOL lenses. For example, one family power is a 19.5 diopter power. A different family power is a 20 diopter power. Conventionally, family powers are tracked in increments of ranges within 0.5 diopters of a half number. Accordingly, any IOL lens falling within a wide range of 0.5 may be designated within a particular family. Because of the wide range, IOL lenses within a particular family may have diopter powers that vary slightly from one another within the range of the family. The IOL cart 104 may be capable of tracking the diopter power of each IOL and of tracking each IOL package with greater precision than has been done in the past. For example, the IOL cart 104 may track individual lenses in addition to or in place of tracking the family of lenses by diopter power. Accordingly, the IOL cart 104 may be configured to track the actual lens power of each IOL stored therein. This will become more apparent in the discussion that follows.

The IOL cart 104 includes a base housing 132 and a computer unit 134 with a display screen 136. The base housing 132 may be formed as a locker, and may include doors 138 that open and close to access inventory contained therein. In this implementation, the doors 138 have windows therein enabling a user to see shelves 142 inside the base housing 132. Other implementations may have solid doors or other types of doors. In this implementation, the base housing 132 includes casters 140 that enable the IOL cart 104 to be moved into and out of a surgical room or to and from other locations as desired.

The computer unit 134 may be used to track inventory within the IOL cart 104. In some implementations, the computer unit 134 dynamically tracks IOL inventory each time the IOL cart 104 is accessed by a user. In addition to tracking inventory, the computer unit 134 may communicate with other components of the surgical suite 100. For example, the computer unit 134 may communicate with the computer unit 108 on the phacoemulsification system 102. For example, the computer unit 134 may display inventory information on the phacoemulsification system's display screen 110 so that the user may have information relating to inventory while using other components of the surgical suite 100. It may show the same or different information on its own display screen 136. In other implementations, the computer unit 134 may convey data or other information to, for example, a surgical microscope. In such implementations, inventory information may be projected onto the viewed image within the microscope so that a user may visualize inventory without looking away from the microscope. It may communicate with or convey information to any surgical system of the surgical suite 100.

Figure 2:
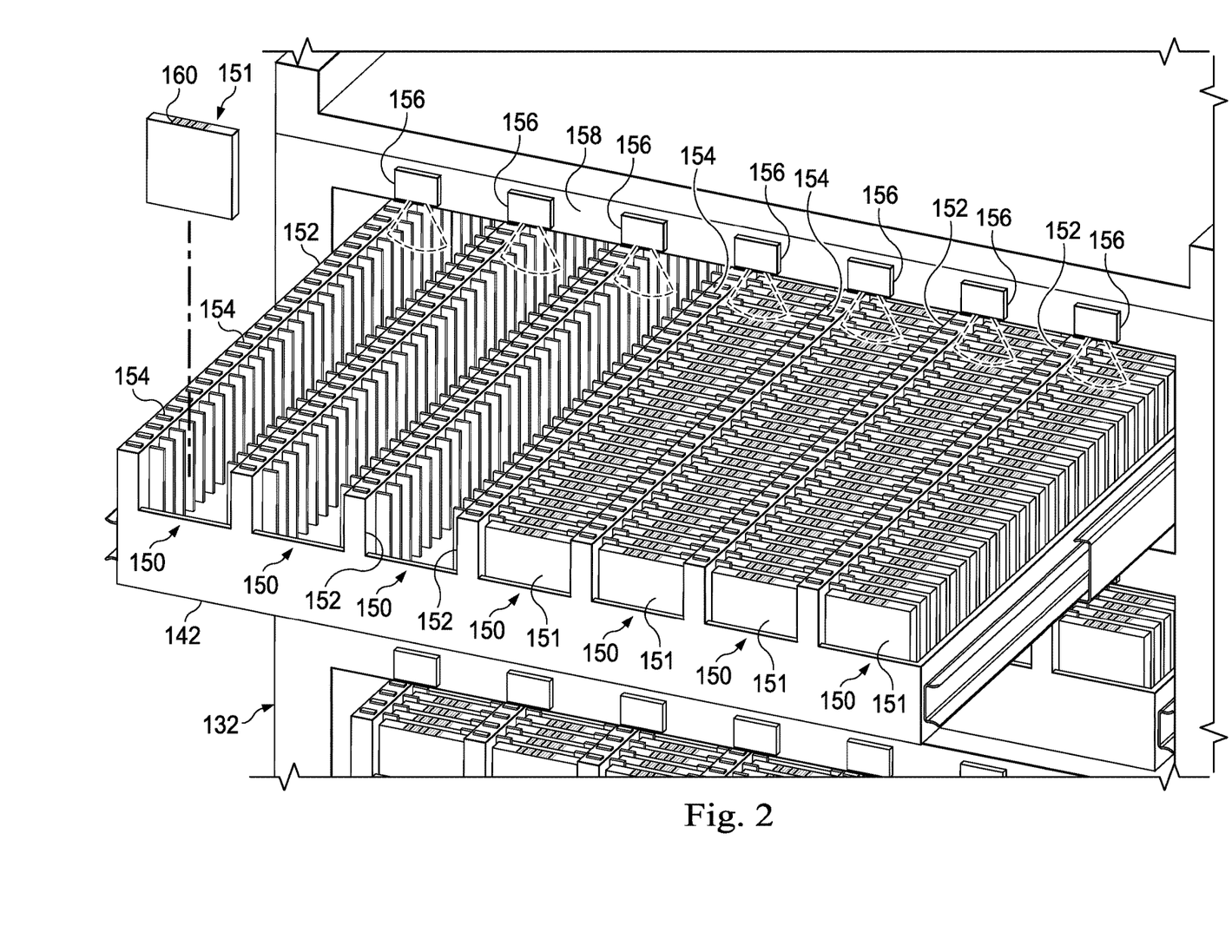
FIG. 2 is an illustration of an exemplary cart of the surgical suite of instruments according to an exemplary aspect.

Additional details of the IOL cart 104 are described with reference to FIG. 2. FIG. 2 shows the IOL cart 104 with the doors 138 open and with a shelf 142 pulled outward to show its contents. In some implementations, the shelf 142 may be formed as a drawer, having sides that protect access and partially enclose the shelf contents. The shelf 142 may slide into and out of the base housing 132 in the same manner that a drawer may be opened and closed. As can be seen, the shelf 142 is formed with a series of rows 150 that may contain a plurality of IOL packages 151. In this implementation, the shelf 142 includes a plurality of walls or separators 152 that separate one row 150 from another. The separators 152 may be spaced any distance apart in order to accommodate standard IOL package sizes.

In the exemplary implementation shown, the separators 152 include visual indicators 154 arranged to align with individual IOL packages 151 in the rows 150. Some implementations include a visual indicator 154 adjacent each individual location that may receive an IOL package 151. The visual indicators 154 may indicate to a user or may identify a specific IOL package. This may help a user locate a specific, desired IOL package to be used during a surgical procedure from among all the IOL packages. Because a desired IOL package 151 may be identified by the visual indicator 154, the user may identify the desired IOL package quickly and with high-efficiency.

In the example shown, the separators 152 include the visual indicators 154. As shown in FIG. 2, the visual indicators 154 are disposed along a top surface of the separators 152. Here, the visual indicators 154 are a series of LED lights that illuminate to identify a desired IOL package among all the IOL packages in the shelf 142. Accordingly, by merely opening the shelf 142, a user may identify a desired IOL package without having to identify and read printing on the IOL package. The visual indicators 154 may operate under the direction of the computer unit 134. Depending on the implementation, the visual indicators 154 may be illuminated to identify a desired IOL package, or may use colored LED lights or other types of indicators to identify a desired IOL package.

Conventionally, surgical staff may be required to potentially flip through or manually look at multiple IOL packages to identify a specific desired IOL package. In so doing, IOL packages may become out of order or may become disorganized. Further, because conventional methods require surgical staff to potentially handle multiple IOL packages, inventory tracking may become more challenging and the potential for misplacement can be relatively high.

The IOL cart 104 is configured to keep a running up-to-date inventory list of IOL packages contained therein. In this implementation, it updates its inventory each time the shelf 142 is opened or closed. This is facilitated by a series of sensors 156 disposed along a frame support structure 158. The support structure 158 may be a part of the base housing 132 or may be a separate support. The sensors 156 may be disposed on an exterior of the support structure 158 in sight of a user, or may be disposed so as to be hidden from a user. The sensors 156 are disposed and configured to read the IOL packages 151 as the IOL packages move past the sensors 156. In some implementations, the sensors 156 are visual scanners or barcode readers that may be formed from light and photo sensors. In some of these implementations, each IOL package 151 includes a barcode on an edge or side that may be read by the sensors 156 when the shelf 142 is opened or closed. In other implementations, the visual scanners may identify or recognize other information on the IOL package 151. This may include systems that detect actual numbers, letters, or other information representing the contents of the IOL package 151. In yet other implementations, the sensors 156 are RFID sensors. In such implementations, each IOL package 151 includes an RFID chip that may be detected by the RFID sensors when the shelf 142 is opened or closed. The barcode or the RFID chip may include specific information about or unique to the IOL in each IOL package 151. For example, among other things, it may include actual IOL power information. Based on the detected IOL packages 151, the computer unit 134 may update a running inventory identifying not only the contents within the IOL cart 104, but also the exact location of all the individual IOL packages 151 in each shelf 142. Accordingly, each time the IOL cart 104 is accessed by a user, the inventory is tracked and updated. In some implementations, the inventory is tracked each time the shelf 142 is closed.

In the implementation shown, one or more sensors 156 are disposed above each row 150. In other implementations, one or more sensors 156 made be disposed at other locations that enable the IOL packages 151 to be observed and scanned. Some implementations include software capability that detects how far the shelf 142 is pulled from the base housing 132, and whether additional IOL packages 151 are within the rows 150 but did not physically pass by the sensors 156 because the shelf was not pulled all the way out. Some implementations include sensors 156 disposed along a front edge of a support structure 158 alignable with a front edge of the shelf 142 and may include additional sensors 156 disposed further inside the base housing 132 to detect IOL packages even when the shelf 142 is not fully pulled out and pushed back into the base housing 132. Other implementations include scanners on movable mechanisms that displace the scanners relative to the IOL packages 151 within the IOL cart 104.

FIG. 2 shows an exemplary IOL package 151 that may be placed within any of the rows 150. As shown, the IOL package 151 includes a barcode 160. The barcode 160 includes data or representative information about the specific IOL within the IOL package 151. This may include information such as a lens power family value as well as specific information relating to the actual lens power of the IOL within the IOL package 151. Accordingly, the IOL package 151 may be marked with specific information relating to the IOL in even greater detail then the IOL lens power family value. For example, if the IOL cart 104 were to include twenty IOL packages 151 all falling within the lens power family value of 19.5, the barcode 160 may include additional information that distinguishes each of the twenty IOL lenses from one another. Accordingly, the barcode 160 may enable each specific lens to be individually tracked by its actual lens power. This may benefit patients by allowing users to identify the IOL lens having a power closest to the lens power that would most benefit a specific patient. In alternative implementations, in place of the barcode 160, the IOL package 151 includes an RFID chip. The chip may include any information that may be conveyed by the barcode sensor discussed above. In yet other implementations, visual scanners may sense, scan or detect other identifying information on the IOL package, including detecting actual printed numbers or letters on the IOL package. Other sensing and detecting methods and systems are also contemplated.

Figure 3:
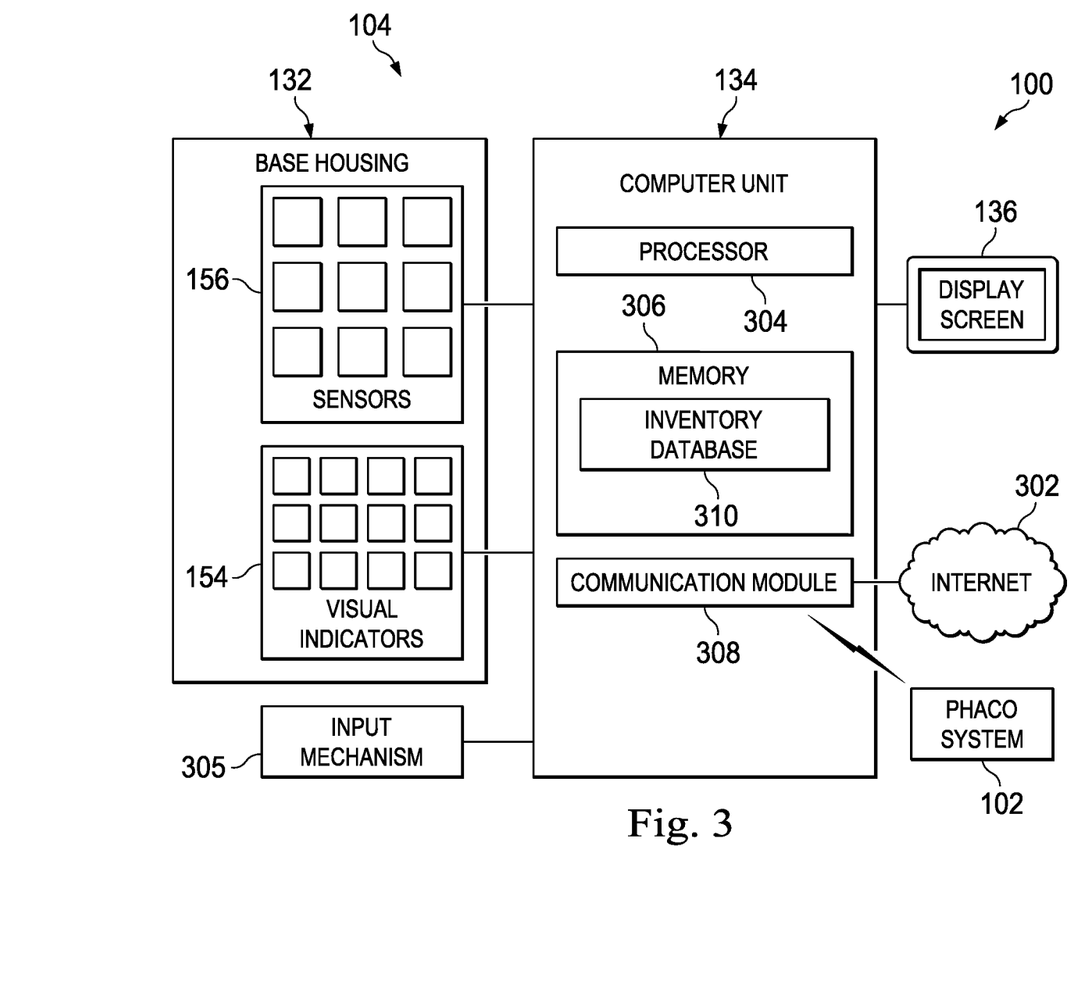
FIG. 3 is an illustration of an exemplary block diagram of a portion of the surgical suite of instruments according to an exemplary aspect.

FIG. 3 is a block diagram showing a portion of the surgical suite 100. It includes the electrical components disposed about the base housing 132 and the computer unit 134 of the IOL cart 104. As can be seen, the computer unit 134 is also in communication with an input mechanism 305, in communication with other surgical systems such as the phacoemulsification system 102, and in communication with networks such as the Internet 302. The computer unit 134 also communicates with the display screen 136. Information relating to the base housing 132, the computer unit 134, or any of the inventory contained within the IOL cart 104, may be displayed on the display screen 136 to a user. The base housing 132 includes the sensors 156 and the visual indicators 154. These operate under the control and direction of the computer unit 134. As such, information relating to IOL packaging that is scanned by the sensors 156 may be communicated from the sensors to the computer unit 134 for processing. The information detected by the sensors 156 may include specific information about the IOL in the IOL package 151, but also may include the location of the IOL package within the base housing 132. More specifically, the sensors 156 may detect the location of the IOL packages 151 on a specific shelf and within a specific row 150 and at a specific location within the row 150. Likewise, in response to a request by a user, the computer unit 134 may identify a specific IOL package for use by controlling the visual indicators 154. That is, when a desired IOL package is identified, the computer unit 134 may activate the indicator 154 adjacent that desired IOL package. Some implementations include a visual indicator for each shelf in the IOL cart 104. Accordingly, a user may observe the visual indicator for the specific shelf, and then may open the shelf to see the visual indicator for the specific IOL package.

The input mechanism 305 is configured to receive input instruction from a user, such as a clinician, surgeon, or other healthcare provider, that may be used to operate the IOL cart, request a lens, or perform other functionality as desired. The input mechanism 305 may be incorporated into the computer unit 134 and may include, for example, a touch screen device responsive to selections made directly on the screen, a standard computer keyboard, a standard pointing device, such as a mouse or trackball, buttons, knobs, or other input devices. Using the input devices, a clinician, surgeon, or other user may make selections of specific IOLs or perform other functions.

The computer unit 134 is configured and arranged to identify and track each IOL package based on information from the sensors 156. It may store information relating to each IOL package in an inventory database that may be accessed when an IOL package is desired for a particular patient. With reference to FIG. 3, the computer unit 134 includes one or more processors 304, a memory 306, and a communication module 308.

The one or more processors 304 may include, for example and without limitation, one or more integrated circuits with power, input, and output pins capable of performing logic functions. In some embodiments, the processor 304 is in communication with the sensors 156 and the visual indicators 154. The processor 304 may receive data or information from the sensors 156, may process the received data or information, and may rely upon it to identify and recommend a specific IOL package to a user. In various implementations, the processor 304 is a targeted device controller. In such implementations, the processor 304 is in communication with and performs specific control functions targeted to the sensors 156 and visual indicators 154. In some implementations, the processor 304 is a microprocessor. In some such cases, the processor 304 is programmable so that it can function to control more than one component of the IOL cart 104. In other cases, the processor 304 is not a programmable microprocessor, but instead is a special purpose controller configured to control different components that perform different functions.

The memory 306 may include various types of memory including volatile memory (such as Random Access Memory (RAM), FRAM, or NAND flash memory) and non-volatile memory (such as solid state storage). The memory 306 interfaces with the processor 304. As such, the processor 304 may write to and read from the memory 306. The memory 306 may store computer readable instructions that include one or more executable programs that when executed by the processor 304, cause the computer unit 134 to perform various functions, including controlling the sensors 156 and actuating specific visual indicators 154 as described herein. The memory 306 may also include executable programs for automatically recognizing when inventory of a particular lens type is low, and automatically placing orders with a distributor or manufacturer of the particular lens type to replenish the inventory.

In this implementation, the memory 306 includes an inventory database 310. The inventory database 310 may include information that is obtained from the sensors 156. In some instances, the inventory database 310 may include information relating to each specific IOL contained within the IOL cart 104. The memory 306 may be updated each time the inventory in the IOL cart 104 changes. In some implementations, the inventory database 310 is updated with IOL information each time a shelf 142 (FIG. 2) is opened or closed. Some implementations update the inventory database 310 only after a shelf is closed. As such, the inventory database 310 may receive information from the processor 304 that is obtained by the sensors 156.

In some implementations, the IOL inventory database 310 may be accessed by a user during a surgical planning phase. Accordingly, based on the preoperative planning, a user may identify a specific IOL for use with a specific patient. The computer unit 134 may be configured to reserve the specific IOL for the specific patient. As such, the specific IOL may be listed as unavailable to other users for other surgeries.

In some implementations, the computer unit 134 may assist the user with preoperative planning by providing an overview of IOL inventory. During the preoperative planning, the computer unit 134 may indicate to the user whether desired IOLs that meet the user's requirements are present in the IOL cart 104. If a desired IOL is present in the IOL cart 104, the IOL cart 104 may permit the user to reserve the IOL for the particular patient. However, if a desired IOL is not present in the IOL cart 104, the IOL cart 104 may assist the user in taking a number of actions. For example, the computer unit 134 may assist the user in placing an order for the desired IOL. In another example, the computer unit 134 may search the IOLs in inventory and identify the IOL having parameters closest to those of the desired IOL. The user may then decide whether to order an IOL or whether to reserve the next closest IOL for the particular patient. Accordingly, the IOL cart 104 may assist the user in preoperative planning as well as during execution of a surgical treatment procedure.

In some implementations the inventory database 310 is a part of the IOL cart 104. However, in other implementations the inventory database 310 is stored separately and apart from the IOL cart 104. For example, the inventory database may be a central database located remote from the IOL cart 104. It may, in some instances, include IOL inventory for multiple IOL carts.

The communication module 308 may enable the computer unit 134 to communicate either directly or via a network with other systems. These systems may include surgical systems that make up the surgical suite 100 (FIG. 1) and may include the phacoemulsification system 102. The systems also may include inventory tracking systems or automated purchasing systems that may simplify the purchase or reservation of additional IOLs when needed. In some implementations, the communication module 308 may transmit inventory information or specific IOL information to the phacoemulsification system 102 display to a user. In so doing, a user performing a procedure with the phacoemulsification system 102 may be able to view information displayed on the phacoemulsification system 102 that relates to the IOL cart 104. This information may include specific lens information including information relating to available lenses and information relating to the lens that is closest to the exact lens desired for a particular patient based on intraoperative evaluation. By providing specific lens information and/or IOL cart information on the phacoemulsification system 102, a user may be able to more efficiently and effectively carry out a surgical procedure.

Likewise, as indicated above, the communication module 308 may enable users to order additional inventory from a manufacturer. In some implementations, the communication module may directly connect the computer unit 134 to an ordering system specifically set up to interface with the IOL cart 104. In some implementations, the IOL cart 104 may automatically place or submit orders with the manufacturer for specific lens types whenever inventory falls below a pre-established threshold. The communication module 308 may communicate with any number of systems and perform any of number of functions over the Internet 302 or other networks. In some implementations, the communication module 308 of the computer unit 134 is configured to communicate wirelessly, while in other implementations the communication module 308 is configured to communicate only via wired connection.

Figure 4:
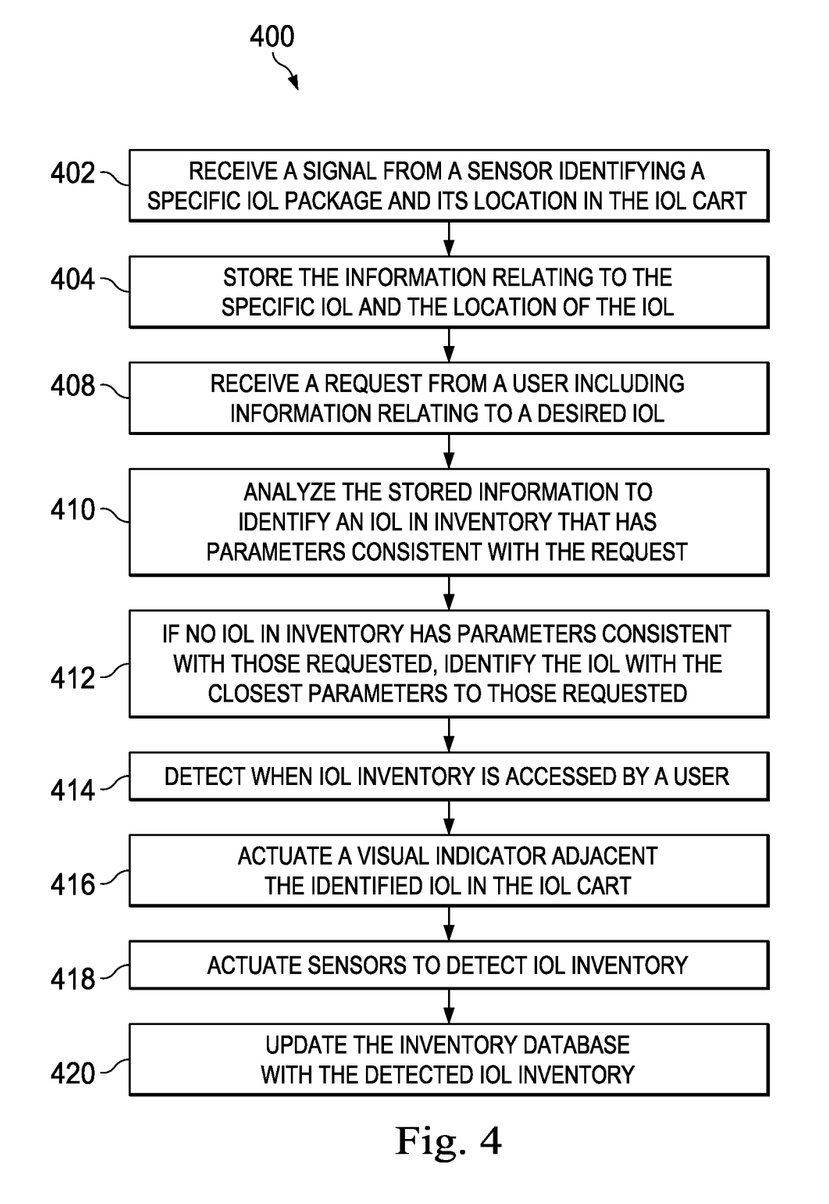
FIG. 4 shows a flow chart of an example method of tracking inventory with the cart of the surgical suite according to an exemplary aspect.

FIG. 4 shows an exemplary method 400 for tracking or maintaining IOL inventory in an IOL cart, such as the IOL cart 104. The method 400 begins at a step 402 of receiving a signal from a sensor identifying a specific IOL package and its location in the IOL cart. The signal received from the sensor may include information relating to the power of each identified IOL. It may include, for example, the family power of the IOL, and may also include the specific or actual power of each IOL lens. It may also include location information for the identified IOL, such as the shelf, row, and location in the row.

The signal may be generated by the sensor in response to identifying the presence of the IOL package. In some implementations herein, the sensor may be activated whenever a shelf is opened or closed on the IOL cart. The sensor may be fixed on the IOL cart while the shelves move in and out past the fixed sensor. As the shelf closes, the sensor may identify all the IOL packages that pass it. In some implementations, each IOL package includes a barcode that is scanned by a barcode reader as it passes the fixed sensor. The signal received from the sensor also includes information about the IOL and location information in the shelf for the IOL. This may include information relating to a specific shelf, row, and location within the row for each IOL package. In other implementations, each IOL package includes an RFID chip that is scanned by an RFID reader as it passes the fixed sensor. In other implementations, the sensor is configured to automatically recognize other symbols or identifying information on the IOL package.

At 404, the received information relating to the specific IOL and the location of the IOL is stored in memory. In some implementations, the information is stored in an inventory database. The stored information may include information about specific IOLs as identified by the sensors, and may also include general information relating to IOLs and the IOL inventory generally. For example, the inventory database may include information relating to the actual power of each IOL, but may also include family power for groups of IOLs. In some implementations, the IOL inventory may include information relating to the number of IOLs in inventory that fall within a particular family power range. For example, in some implementations the IOL inventory may indicate to a user that there are, for example only, five IOLs within the power range of 19.5. In other implementations, the IOL inventory may indicate to a user the specific, actual powers of each IOL lens with a much greater specificity than the family power.

At 408, the computer unit may receive a request from a user that includes information relating to a desired IOL. In some instances, the information may come as a result of a preoperative assessment of the patient. In the surgical planning phase, a user may desire to know the powers of IOLs currently in inventory. As indicated herein, in some implementations, these may be reserved for use for a particular patient. This may be done using the input mechanism to select and reserve a specific IOL from the IOL inventory.

In other instances the computer unit may receive a request from a user performing an intraoperative assessment. This may occur when, during the intraoperative measurements, the user realizes that the best IOL for the patient undergoing surgery is different than the planned IOL. In such a situation, the user may input a request to the IOL cart for an IOL having a specific power.

In response to the request from the user, at 410 the computer system analyzes the stored information in the inventory database to identify an IOL having a power or other parameters consistent with the request. The computer system may compare the requested IOL to each IOL in the IOL cart. In some implementations, the computer system may compare the requested IOL to IOLs in other IOL carts within the same facility. When a matching IOL is found in the IOL cart, the computer system may inform the user using the display screen.

If none of the IOLs in inventory has parameters consistent with those requested, then the computer system identifies the IOL with the closest parameters to those requested. The parameters, including the family power and the actual power of the IOL may be displayed to a user for selection. In some implementations, multiple IOLs may be identified and displayed to a user with a recommendation of one IOL over the others. The user may then select the recommended IOL or a different IOL depending upon the user's preference. With the IOL selected from the inventory, whether automatically by the computer system or by a user input at the computer system, the system may indicate to the user that the IOL may be accessed and removed from the IOL cart. In some implementations, the computer system may indicate the IOL location by shelf, row, and location within the row.

At 414, the computer system detects when the IOL inventory is accessed by a user. The computer system may do this using the sensors 156 and or other sensors disposed about the IOL cart. In some implementations, the computer system detects access by a user by monitoring whether a shelf is being displaced. For example, when the shelf is displaced relative to the sensors, signals from the sensors may indicate to the computer system that the IOL inventory is being accessed.

At 416, the computer system may actuate a visual indicator adjacent the selected IOL in the IOL cart. This may include actuating an LED light adjacent the IOL package containing the desired IOL. Accordingly, a user may easily identify the correct IOL for the patient by simply opening the shelf and looking at the visual indicator. Although described as a light, other visual indicators may be used. For example, mechanical systems may be used to present the selected IOL to the user. This may include dispensing the IOL package or otherwise physically displacing the package from other IOL packages in the IOL cart. Some implementations include visual indicators that identify the shelf as well as the row and location in the row.

At 418 the computer system may actuate the sensors to detect the IOL inventory because it may have changed when the shelf was accessed. Sensor actuation may automatically occur any time the shelf is displaced. In some implementations, sensor actuation occurs only when the shelf is being returned to its storage position which may be a fully pushed in position. As such, the shelf may be monitored for movement and the sensors may be activated when movement is detected. In other implementations, the sensors are always on. Other triggers for activating automatic scanning of the inventory are also contemplated. With the sensors actuated, the IOL cart is in condition to detect each IOL package contained within the shelf of the IOL cart. As such, as the shelf is pushed into the cart, the IOL packages within the shelf move past the sensors. The sensors may detect the IOL packages as they move past, and may send signals representing information from the IOL packages to the processor and inventory database. In some implementations, the sensors are barcode scanners and each IOL package includes a barcode that represents information relating to the IOL. In other implementations, the sensors are RFID sensors and each IOL package includes an RFID chip that includes information relating to the IOL. In yet other implementations, the sensors are configured to automatically recognize other symbols or identifying information on the IOL package. For example, the information may include the family power for the IOL and may also include the actual power of the IOL. Other information may also be included such as date of manufacture, brand, type, dimensional information, and other IOL parameter information.

At 420, the processor of the computer system updates the inventory database to include the information obtained from the scanners. Accordingly, the inventory database includes accurate information relating to the IOL inventory. In the exemplary implementation described, each time the inventory is accessed by a user, the inventory database is updated. In some instances, a user may remove multiple IOL packages from the IOL cart. When the shelf is pushed in, the IOL inventory database will be updated to accurately reflect the IOL packages within the cart. As such, the inventory database maintains a relatively dynamic and accurate assessment of IOL packages within the IOL cart. Furthermore, if a user were to mistakenly remove the wrong IOL package, the inventory database is accurately updated to reflect only the IOLs remaining within the IOL cart. In some implementations, however, the computer system is configured to display a visual indicator on the computer system display screen if an IOL is removed from the IOL cart that was not selected by the user. This may help ensure that the user has removed the correct IOL from the cart and reduce the risk of the user implanting an undesirable IOL.

While the IOL cart has been described as cooperating with other surgical systems in a surgical suite system, such as the phacoemulsification system, yet other devices may cooperate with the IOL cart. For example, in some implementations, the IOL cart may cooperate with systems for intraoperative modification of lens design or lens manufacture. For example, some implementations may enable the IOL cart to communicate directly with a laser system that may modify lenses to a desired power intraoperatively for implantation in the patient. In such instances, the lenses may be formed from a blank or solid lens material based on parameters and values input into the IOL cart system. In yet other implementations, the IOL cart may cooperate with a 3-D printer arranged and configured to generate an implantable lens based purely on the lens parameters input and desired at the IOL cart. As such, the IOL cart may become an integral component in lens selection and modification because it has data prior to surgery from preoperative planning as well as data directly from the intraoperative evaluation results necessary for the creation of the custom IOL.

Accordingly the IOL cart may organize IOL power selection and generate planning and operating room efficiencies by connecting surgical planning and execution with IOL access.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An intraocular lens (IOL) housing comprising:
 a base for receiving a plurality of IOL packages;
 one or more RFID sensors configured to detect a presence of individual IOL packages and a diopter power associated with each IOL package;
 a movable shelf arranged to carry the plurality of IOL packages, wherein the one or more RFID sensors are positioned above the moveable shelf to detect the IOL packages; and
 a processor associated with the base and configured to receive, from the one or more RFID sensors, dynamic IOL inventory management information, the dynamic IOL inventory management information relating to a number of the IOL packages disposed within the base and a diopter power of each of the IOL packages disposed within the base, the processor being further configured to provide the dynamic inventory management information to an inventory database management system stored in a network-based storage location.

2. The IOL housing of claim 1, wherein the processor is further configured to automatically place orders with a distributor or manufacturer of a particular lens type to replenish the inventory when a specific lens type fall below a predetermined threshold.

3. The IOL housing of claim 1, wherein the processor is further configured to instruct the inventory database managed system to automatically place orders with a distributor or manufacturer of a particular lens type to replenish the inventory when a specific lens type fall below a predetermined threshold.

4. The IOL housing of claim 1, wherein the one or more sensors are disposed in a position to scan IOL packages as they are replenished into the base.

5. The IOL housing of claim 1, further comprising:
 a plurality of visual indicators actuatable by the processor, wherein in the IOL inventory management information further comprises a location for each of the IOL packages in the housing, and wherein the processor is further configured to receive a request from a user relating to a desired IOL, compare the IOL inventory management information to the received request related to a desired IOL, select an IOL package with a diopter power associated IOL power information closest to a desired IOL power, and cause one or more of the plurality of visual indicators to actuate adjacent to the location of the IOL package with the diopter power closest to the desired IOL power.

6. The IOL housing of claim 5, wherein the plurality of visual indicators are LED lights.

7. The IOL housing of claim 1, wherein the base comprises a shelf divided into rows sized and arranged to receive individual IOL packages, wherein the shelf comprises a plurality of separators that divide the shelf into the rows, each separator having one or more visual indicators usable to identify an IOL package disposed thereon.

* * * * *